United States Patent
Yoshikawa et al.

(10) Patent No.: US 6,174,864 B1
(45) Date of Patent: Jan. 16, 2001

(54) METHODS FOR THE PREVENTION OR TREATMENT OF INFLAMMATORY BOWEL DISEASES

(75) Inventors: Toshikazu Yoshikawa; Norimasa Yoshida, both of Kyoto; Hironobu Murase, Gifu, all of (JP)

(73) Assignee: CCI Corporation (JP)

( * ) Notice: Under 35 U.S.C. 154(b), the term of this patent shall be extended for 0 days.

(21) Appl. No.: 09/319,647

(22) PCT Filed: Dec. 10, 1997

(86) PCT No.: PCT/JP97/04544

§ 371 Date: Aug. 9, 1999

§ 102(e) Date: Aug. 9, 1999

(87) PCT Pub. No.: WO98/25629

PCT Pub. Date: Jun. 18, 1998

(30) Foreign Application Priority Data

Dec. 10, 1996 (JP) ............................................... 8-329901

(51) Int. Cl.[7] ................................................... A61K 31/70
(52) U.S. Cl. ................................................... 514/28; 514/27
(58) Field of Search ................................... 514/28, 27

(56) References Cited

U.S. PATENT DOCUMENTS

| | | | |
|---|---|---|---|
| 5,294,630 | 3/1994 | Blake et al. | 514/372 |
| 5,629,337 | 5/1997 | Gray | 514/443 |
| 5,639,770 | 6/1997 | Chihiro et al. | 514/365 |

FOREIGN PATENT DOCUMENTS

| | | |
|---|---|---|
| 0 611 152 A1 | 2/1994 | (EP) . |
| 0 640 609 A1 | 8/1994 | (EP) . |
| 0 731 099 A1 | 2/1996 | (EP) . |
| 5-246847 | 9/1993 | (JP) . |
| 5-294834 | 11/1993 | (JP) . |
| 6-65222 | 3/1994 | (JP) . |
| 6-157310 | 6/1994 | (JP) . |
| 7-112980 | 5/1995 | (JP) . |
| 7-118287 | 5/1995 | (JP) . |
| 07118287 * | 5/1995 | (JP) . |
| 7-316150 | 12/1995 | (JP) . |
| 8-253466 | 1/1996 | (JP) . |
| 8-510253 | 10/1996 | (JP) . |

\* cited by examiner

Primary Examiner—Theodore J. Criares
Assistant Examiner—Jennifer Kim
(74) Attorney, Agent, or Firm—Mathews, Collins, Shepherd & Gould, P.A.

(57) ABSTRACT

A preventive and curative agent for inflammatory bowel diseases is disclosed which has as an active ingredient thereof a chromanol glucoside represented by the following general formula (1)

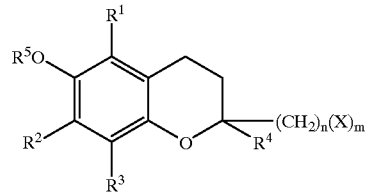

(1)

(wherein $R^1$, $R^2$, $R^3$, and $R^4$ represent identically or differently either a hydrogen atom or a lower alkyl group, $R^5$ represents a hydrogen atom, a lower alkyl group, or a lower acyl group, X represents a monosaccharide residue or an oligosaccharide residue having the hydrogen atom in the hydroxyl group thereof optionally substituted with a lower alkyl group or a lower acyl group, n represents an integer of 0–6, and m represents an integer of 1–6).

Owing to the use, as an active ingredient, of the chromanol glucoside excelling in water solubility and possessing an oxidization resisting action and a free radical resisting action, the agent can conspicuously repress the lesion of an inflammatory bowel disease and prominently ameriolate the condition of disease. It can be manufactured into an aqueous preparation containing the active ingredient in a high concentration and, therefore, act effectively on the seat of disease at a low application rate, and prevent and cure the inflammatory bowel diseases. It further allows very safe use because it entails no side effect.

5 Claims, No Drawings

METHODS FOR THE PREVENTION OR TREATMENT OF INFLAMMATORY BOWEL DISEASES

TECHNICAL FIELD

This invention relates to a novel preventive and curative agent for inflammatory bowel diseases. More particularly, this invention relates to a preventive and curative agent for inflammatory bowel diseases, using a water-soluble chromanol glucoside as an active ingredient.

BACKGROUND ART

The organism is inhabited by antioxidizing enzymes and antioxidizing substances that function to prevent pathologically excessive occurrence of free radicals or eliminate the free radicals suffered to occur at all. It is known that on the intestinal mucous membranes of patients of such inflammatory bowel diseases as ulcerative colitis and Crohn's disease, such antioxidizing enzymes and antioxidizing substances as superoxide dismutase (SOD), glutathione, and α-tocopherol are consumed till shortage of supply (G. G. Buffinton and W. F. Doe: Free Radic. Biol. Med., 19 (1995) 911–918). It is believed that the reinforcement of the antioxidation protecting system by the administration of a medicine capable of resisting oxidation is effective in preventing and curing these diseases.

The free radicals, as aptly called a "double-edged sword," not only function to give rise to a morbid condition but also prove very important for a biophylactic system. Mere elimination of all the free radicals is hardly feasible. This fact constitutes itself the largest cause for making difficult the clinical application of the free radical resistance therapy.

Of the medicines which possess an antioxidizing action, those which have been already accepted for clinical application as an internal curative agent for ulcerative colitis and Crohn's disease include classic steroid chemicals and salazosulfapyridine (SASP, Salazopyrin) and those which have been undergoing a basic study include SOD preparations such as Mn-SOD and CuZn-SOD, zinc preparations such as allopurinol and porapurezinc [sic], α-tocopherol, glutathione, glutathione peroxidase, and 21-aminosteroid, herbal medicines such as sigyakusan [sic] and rebamipido [sic].

Particularly, (α-tocopherol is a typical entity of vitamin E, possesses a function of eliminating free radicals by supplying a hydrogen atom from the hydroxyl group at the 6 position of a chromane ring thereof, and has earned fame as an antioxidizing agent.

The vitamin E, however, is a viscous oily substance not soluble in water because it has a long-chain hydrocarbon group (phytyl group) in the molecular unit thereof. When the vitamin E is to be administered for the purpose of repressing and controlling the free radicals in the organism, therefore, it betrays a fatal disadvantage of not allowing itself to be used in the form of a solution like an internal medicine or an injection. To overcome this weak point, 6-hydroxy-2,5,7,8-tetramethylchroman-2-carboxylic acid which is endowed with water-solubility by the substitution of the phytyl group at the 2 position with a carboxyl group has been developed. It is commercially offered as a water-soluble antioxidizing agent under the designation of "Trolox." The water-solubility of this agent is extremely low (about 15 mg/100 ml) and fails to achieve full satisfaction. For the same reason, 2-hydroxymethyl-2,5,7,8-tetramethylchroman-6-ol resulting from the substitution of the phytyl group at the 2 position with an alcohol (hereinafter referred to as "TMC-2-substituted methanol") has been developed. This TMC-2-substituted methanol possesses water-solubility of about 100 mg/100 ml, a value about 6.3 times that of Trolox. In spite of this relatively high water-solubility, the administration of 1 g of this compound to a patient, for example, requires the compound to be used as dissolved in such a large amount of water as 1 liter. The TMC-2-substituted methanol, therefore, still encounters the problem of offering no fully satisfactory water-solubility.

This invention, produced in view of the problem of prior art described above, has for an object thereof the provision of a novel preventive and curative agent for inflammatory diseases, which manifests the effect at a low application rate without entailing a side effect in preventing the inflammatory diseases or ameliorating and curing them.

Another object of this invention is to provide a novel preventive and curative agent for inflammatory bowel diseases, which possesses a fine antioxidizing action such as to bring effective repression and control of a free radical reaction possibly occurring on the intestinal mucous membrane at the site of an inflammatory bowel disease.

Still another object of this invention is to provide a novel preventive and curative agent for inflammatory bowel diseases, which is capable of repressing development of cell adhesion molecules and reducing humectation of the tissue with neutrophil.

Yet another object of this invention is to provide a novel preventive and curative agent for inflammatory bowel diseases, which can be formulated as an aqueous preparation containing the active ingredient thereof in a high concentration.

DISCLOSURE OF THE INVENTION

The present inventors formerly succeeded in synthesizing a chromanol glucoside possessing high water-solubility by binding sugar to the hydroxyl group at the 2 position of the TMC-2-substituted alcohol deficient in water-solubility (JP-A-07-118,287). This time, they have made a surprising discovery that the preventive and curative agent for inflammatory bowel diseases which has the chromanol glucoside as the active ingredient thereof possesses an action of repressing development of cell adhesion molecules and significantly reducing humectation of the intestinal tissues with neutrophil in addition to a fine antioxidizing action and free radical resisting action and, therefore, proves highly effective in preventing and curing such inflammatory bowel diseases as ulcerative colitis and Crohn's disease. The present invention has been perfected on the basis of this knowledge.

Specifically, this invention concerns a preventive and curative agent for inflammatory bowel diseases having as an active ingredient thereof a chromanol glucoside represented by the following general formula (1)

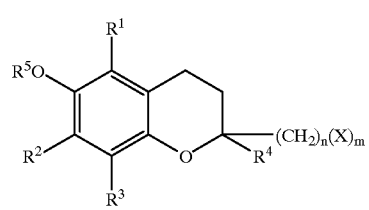

(1)

(wherein $R^1$, $R^2$, $R^3$, and $R^4$ represent identically or differently either a hydrogen atom or a lower alkyl group, $R^5$ represents a hydrogen atom, a lower alkyl group, or a lower acyl group, X represents a monosaccharide residue or an oligosaccharide residue having the hydrogen atom in the hydroxyl group thereof optionally substituted with a lower alkyl group or a lower acyl group, n represents an integer of 0–6, and m represents an integer of 1–6).

This invention further concerns the preventive and curative agent for inflammatory bowel diseases mentioned above, wherein the chromanol glucoside mentioned above is 2-(α-D-glucopyranosyl)methyl-2,5,7,8-tetramethylchroman-6-ol.

This invention further concerns the preventive and curative agent for inflammatory bowel diseases mentioned above, wherein the inflammatory bowel disease is an ulcerative colitis or Crohn's disease.

This invention further concerns the preventive and curative agent for inflammatory bowel diseases mentioned above, wherein the agent is an aqueous preparation.

BEST MODE OF EMBODYING THE INVENTION

The preventing and curative agent of the present invention for inflammatory bowel diseases is characterized by having as an active ingredient thereof a chromanol glucoside represented by the following general formula (1)

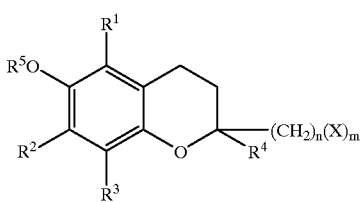

(1)

(wherein $R^1$, $R^2$, $R^3$, and $R^4$ represent identically or differently either a hydrogen atom or a lower alkyl group, $R^5$ represents a hydrogen atom, a lower alkyl group, or a lower acyl group, X represents a monosaccharide residue or an oligosaccharide residue having the hydrogen atom in the hydroxyl group thereof optionally substituted with a lower alkyl group or a lower acyl group, n represents an integer of 0–6, and m represents an integer of 1–6).

In the general formula (1) mentioned above, the lower alkyl groups for $R^1$, $R^2$, $R^3$, $R^4$, and $R^5$ are properly lower alkyl groups of 1–8, preferably 1–6, carbon atoms. As concrete examples of the alkyl groups, methyl group, ethyl group, propyl group, isopropyl group, butyl group, isobutyl group, pentyl group, isopentyl group, hexyl group, heptyl group, and octyl group may be cited. Among other lower alkyl groups mentioned above, methyl group or ethyl group proves particularly advantageous. The lower acyl groups for $R^5$ are properly lower acyl groups of 1–8, preferably 1–6, carbon atoms. As concrete examples of the acyl groups, formyl group, acetyl group, propionyl group, butyryl group, isobutyryl group, valeryl group, isovaleryl group, pivaloyl group, hexanoyl group, heptanoyl group, and octanoyl group may be cited. Among other lower acyl groups mentioned above, acetyl group, propionyl group, or butyryl group proves particularly advantageous. The monosaccharide residues for X include such sugar residues as glucose, galactose, fucose, xylose, mannose, rhamnose, arabinose, lyxose, ribose, allose, altrose, idose, talose, deoxyribose, 2-deoxyribose, quinovose, and abequose, for example. The oligosaccharide residues for X include unions of two to four monosaccharides mentioned above, i.e. such sugar residues as maltose, lactose, cellobiose, raffinose, xylobiose, and sucrose, for example. Among other saccharide residues mentioned above, glucose, galactose, fucose, xylose, and rhamnose prove particularly advantageous. The hydrogen atom of the hydroxyl group in the sugar residue of X may be substituted with a lower alkyl group, preferably a lower alkyl group of 1–8 carbon atoms, or with a lower acyl group, preferably a lower acyl group of 1–10 carbon atoms. Further, n represents an integer of 0–6, preferably 1–4 and m an integer of 1–6, preferably 1–3. As preferred concrete examples of the chromanol glucoside represented by the general formula (1), 2-(α-D-glucopyranosyl)methyl-2,5,7,8-tetramethylchroman-6-ol, 2-(α-D-galactopyranosyl)methyl-2,5,7,8-tetramethyl-chroman-6-ol, 2-(β-L-fucopyranosyl)methyl-2,5,7,8-tetramethylchroman-6-ol, 2-(α-L-rhamnopyranosyl)methyl-2,5,7,8-tetramethylchroman-6-ol, and 2-(β-D-xylopyranosyl)methyl-2,5,7,8-tetramethylchroman-6-ol may be cited.

The chromanol glucoside for use in this invention can be produced by an enzymatic reaction which comprises causing a 2-substituted alcohol represented by the following general formula (2):

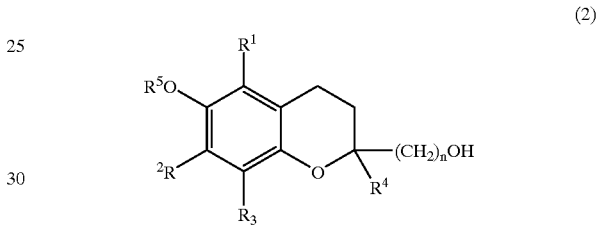

(2)

(wherein $R^1$, $R^2$, $R^3$, $R^4$, and $R^5$ and n have the same meanings as defined above) to react with an oligosaccharide, soluble starch, starch, or cyclodextrin in the presence of an enzyme catalyzing a relevant sugar transfer action thereby specifically binding a specific hydroxyl group of sugar to the hydroxyl group at the 2 position of the 2-substituted alcohol in accordance with the method disclosed in JP-A-07-118, 287, for example (Enzyme Method).

The 2-substituted alcohol represented by the general formula (2) which is used as the raw material for the reaction mentioned above (hereinafter referred to simply as "2-substituted alcohol") is a known substance which can be obtained by any of the methods disclosed in JP-B-01-43,755 and JP-B-01-49,135, for example. The 2-substituted alcohol which has methyl groups severally for $R^1$, $R^2$, $R^3$, and $R^4$, a hydrogen atom for $R^5$, and 1 for n in the general formula (2), for example, can be easily obtained as by refluxing Trolox in diethyl ether in the presence of lithium aluminum hydride.

The enzymes to be used in the aforementioned reaction for catalyzing the action of sugar transfer are preferred to be differentiated, depending on the kind of sugar to be used in the reaction, as follows.

(1) The linkage of a glucose residue to the 2-substituted alcohol with an α-bond (a) The maltooligosaccharide at the position of maltose through maltotetraose is preferred to be acted on by an α-glucosidase, EC3.2.1.20). The α-glucosidase to be used may be any of the species originating in virtually all sources. As concrete examples of the α-glucosidase, the α-glucosidase originating in Saccharomyces sp. made by Toyobo Co., Ltd., the α-glucosidase originating in Saccharomyces cerevisiae made by Oriental Yeast Co., Ltd., the α-glucosidase originating in Aspergillus niger made by Amano Pharmaceutical Co., Ltd., the aglucosidase originating in Saccharomyces sp. made by Wako Pure Chemical Industries, Ltd., and the α-glucosidase originating in Baker's yeast and the α-glucosidase originating in Bacillus sp. made by Sigma Chemical Co. may be cited.

(b) The soluble starch or starch is preferred to be acted on by a 4-α-glucanotransferase (EC2.4.1.25).

(2) The linkage of a glucose residue or a maltooligosaccharide residue to the 2-substituted alcohol with an α-bond (a) The maltooligosaccharide, soluble starch, starch, or cyclodextrin (α, β, γ) is preferred to be acted on by cyclomaltodextrin glucanotransferase, EC2.4.1.19). As typical examples thereof, the cyclodextrin glucano-transferase originating in Bacillus macerans made by Amano Pharmaceutical Co., Ltd. and the cyclodextrin glucano transferase originating in Bacillus stearothermophilus made by Hayashibara biochemical Laboratories, Inc. and other cyclodextrin glucanotransferases originating in Bacillus megaterium and Bacillus circulans ATCC 9995 may be cited.

(3) The linkage of a glucose residue to the 2-substituted alcohol with a β-bond (a) The oligosaccharide formed of such a β-bond as cellobiose, curdlan, or laminaran is preferred to be acted on by a β-glucosidase (EC3.2.1.21).

(b) The cellobiose placed in the presence of phosphoric acid is preferred to be acted on by a cellobiose phosphrylase (EC2.4.1.20).

(4) The linkage of a galactose residue to the 2-substituted alcohol with an αbond (a) The melibiose or the raffinose is preferred to be acted on by an galactosidase (EC3.2.1.22).

(5) The linkage of a galactose residue to the 2-substituted alcohol with a β-bond (a) The lactose or the like is preferred to be acted on by a β-galactosidase (EC3.2.1.23).

(b) The arabinogalactane or the like is preferred to be acted on by an endo-1,4-β-galactanase (EC3.2.1.89).

(6) The linkage of a fructose residue to the 2-substituted alcohol with a β-bond (a) The sucrose, raffinose, melibiose, or the like is preferred to be acted on by a levansucrase (EC2.4.1.10).

(b) The sucrose is preferred to be acted on by a β-fructofuranosidase (EC3.2.1.26).

(c) The inulin or the like is preferred to be acted on by an inulin fructotransferase (EC2.4.1.93).

The reaction conditions to be adopted in the aforementioned reaction are variable with the species of chromanol glucosidase and enzyme to be used. When a chromanol glucoside having 1 for m in the general formula (1) is synthesized by the use of α-glucosidase, for example, the 2-substituted alcohol is preferred to be dissolved in a sugar solution. For the purpose of this solution, it is proper to add an organic solvent. As concrete examples of the organic solvent, dimethyl sulfoxide, N,N-dimethyl formamide, methanol, ethanol, acetone, and acetonitrile may be cited. In consideration of the factor of heightening the activity of transferring αglucosidase, dimethyl sulfoxide or N,N-dimethyl formamide is preferably used. The concentration of the organic solvent to be added is in the range of 1–50 (v/v) %. When the efficiency of reaction merits due consideration, this concentration is preferred to be in the range of 5–35 (v/v) %.

The concentration of the 2-substituted alcohol is properly equal or close to the saturated concentration thereof in the reaction solution. The kind of sugar to be used is properly that of such a low molecular weight as to range from maltose to maltotetraose. Preferably, this sugar is maltose. Properly, the concentration of the sugar is in the range of 1–70 (w/v) %, preferably 30–60 (w/v) %. The pH is in the range of 4.5–7.5, preferably 5.0–6.5. The reaction temperature is in the range of 10–70° C., preferably 30–60° C. The reaction time is in the range of 1–40 hours, preferably 2–24 hours. Of course, these conditions are affected by such factors as, for example, the amount of enzyme to be used. After the reaction is completed, the chromanol glucoside aimed at is obtained in a state having a high assay by treating the produced reaction solution by column chromatography using "XAD" (sold by Organo Co., Ltd.) as a carrier.

When a chromanol glucoside having 1 for m in the general formula (1) is to be synthesized by using cyclomaltodextrin glucanotransferase, for example, the reaction is preferred to rely on the solution of the 2-substituted alcohol in a sugar solution. For the purpose of this solution, the addition of an organic solvent proves preferable. As concrete examples of the organic solvent, dimethyl sulfoxide, N,N-dimethyl formamide, methanol, ethanol, acetone, and acetonitrile may be cited. The concentration of the organic solvent to be added is in the range of 1–50 (v/v) %. When the efficiency of reaction merits due consideration, this concentration is preferred to be in the range of 5–35 (v/v) %. The concentration of the 2-substituted alcohol is properly equal or close to the saturated concentration thereof in the reaction solution.

As concrete examples of the kind of sugar to be preferably used in the reaction mentioned above, maltooligosaccharides having a polymerization degree exceeding that of maltotriose, soluble starch, starch, and cyclodextrins (α, β, γ) may be cited. The concentration of the sugar is 1–70 (w/v) %, preferably 5–50 (w/v) %. The pH is in the range of 4.5–8.5, preferably 5.0–7.5. The reaction temperature is in the range of 10–70° C., preferably 30–60° C. The reaction time is in the range of 1–60 hours, preferably 2–50 hours. It is provided, however, that these conditions are affected by the amount of an enzyme to be used. The chromanol glucosidase to be obtained by the reaction performed as described above is a mixture having about 1 to 8 for m in the general formula (1). Then, by treating this mixture with glucoamylase (EC3.2.1.3), it is made possible to obtain exclusively the chromanol glucoside having 1 for m in the general formula (1). In this case, the reaction temperature is in the range of 20–70° C., preferably 30–60° C. and the reaction time in the range of 0.1–40 hours, preferably 1–24 hours. It is provided, however, that these conditions are affected by the amount of an enzyme to be used. Then, by subjecting the solution resulting from the aforementioned treatment with glucoamylase to column chromatography using "XAD" (Organo Co., Ltd.) as a carrier, the chromanol glucoside having 1 for m in the general formula (1) is obtained in a state having a high assay.

When a chromanol glucoside having 2 for m in the general formula (1) is to be produced, a chromanol glucoside having 1 or 2 for m in the general formula (1) is exclusively obtained by causing a β-amylase (EC3.2.1.2) to react with a chromanol glucoside obtained in the form of a mixture having about 1 to 8 for m in the general formula (1) by employing the same conditions as described above while using cyclomaltodextrin glucanotransferase instead. At this time, the reaction temperature is in the range of 20–70° C., preferably 30–60° C. The reaction time is in the range of 0.1–40 hours, preferably 1–24 hours. It is provided, however, that these conditions are affected by the amount of an enzyme to be used. By subjecting the solution resulting from the treatment with the β-amylase to column chromatography using "XAD" (Organo Co., Ltd.) as a carrier, the chromanol glucoside having 2 for m in the general formula (1) is obtained in a state having a high assay and, at the same time, a chromanol glucoside having 1 for m in the general formula (1) is obtained.

When a chromanol glucoside having not less than 3 for m in the general formula (1) is to be produced, chromanol glucosides having varying values of m can be obtained each with a high assay by subjecting chromanol glucosides of the form of a mixture having about 1 to 8 for m in the general formula (1) obtained by adopting the same conditions as described above while using cyclomaltodextrin glucanotransferase to separation chromatography using HPLC.

The preferred embodiment, as described above, binds a glucose residue or a maltooligosaccharide residue as a sugar residue to the 2-substituted alcohol. Alternatively, the present invention can be preferably embodied in a mode of binding a galactose residue as a sugar residue to the 2-substituted alcohol. In this mode, the chromanol glucoside aimed at can be obtained in a high assay by following the procedure of the embodiment described above while using a β-galactosidase as an enzyme when lactose is used as a sugar or an endo-1,4-β-galactanase as an enzyme when arabinogalactane is used as a sugar according to the principle described in the paragraph describing the enzyme for catalyzing the action of sugar transfer.

The chromanol glucoside to be used in this invention can be otherwise produced by subjecting a 2-substituted alcohol having the hydroxyl group at the 6 position protected with a protective group (hereinafter referred to as "sugar receptor") and a sugar derivative having a leaving group introduced to the anomer position and having the other hydroxyl groups protected each with a protective group (hereinafter referred to as "sugar donor") to a condensation reaction in accordance with the method described in JP-A-09-77,918 (organic synthesis method).

As concrete examples of the protective group for protecting the hydroxyl group at the 6 position of the sugar receptor for use in the reaction mentioned above, acetyl group, benzoyl group, pivaloyl group, chloroacetyl group, levulinoyl group, benzyl group, p-methoxybenzyl group, allyl group, t-butyldimethylsylyl group, t-butyldiphenylsylyl group, trimethylsylyl group, and trityl group may be cited. Among other protective groups mentioned above, acetyl group and benzoyl group are particularly preferable.

As concrete examples of the leaving group to be introduced into the anomer position of the sugar donor for use in the reaction mentioned above, halogen atoms such as chlorine, bromide, and fluorine, sulfur compounds such as thiomethyl group, thioethyl group, and thiophenyl group, and trichloroacetoimide group may be cited. Among other leaving groups mentioned above, bromine, chlorine, thiomethyl group, thioethyl group, thiophenyl group, and trichloroacetoimide group prove particularly advantageous. As concrete examples of the protective group for protecting the hydroxyl groups other than those at the anomer position, acyl type protective groups such as acetyl group, benzoyl group, pivaloyl group, chloroacetyl group, and levulinoyl group and ether type protective groups such as benzyl group, p-methoxybenzyl group, allyl group, t-butyldimethylsylyl group, t-butyldiphenylsylyl group, trimethylsylyl group, and trityl group may be cited. Among other protective groups mentioned above, acyl type protective groups, especially acetyl group, prove particularly advantageous.

The sugar donor of the nature described above can be easily prepared by introducing protective groups respectively to all the hydroxyl groups and then substituting the anomer positions with leaving groups in accordance with the universally known method.

Specifically, the condensation reaction of the sugar receptor and the sugar donor mentioned above begins by dissolving the sugar receptor and the sugar donor in a nonpolar solvent. Properly, the amounts of the sugar receptor and the sugar donor to be charged are such that the molar ratio of the sugar donor to the sugar receptor is in the range of 1.0–1.5, preferably 1.1–1.3. As concrete examples of the nonpolar polar solvent, methylene chloride and benzene may be cited.

Then, the condensation reaction of the sugar donor and the sugar receptor is carried out under an anhydrous condition in the presence of an activating agent. As concrete examples of the activating agent, trifluoroboric acid ether complex, silver perchlorate, silver trifluoromethanesulfonate, silver bromide, silver cyanide, N-iodosuccinic acid imide-trifluoromethane-sulfonic acid, dimetyhyl(methylthio)sulfonium tiflate, and p-toluenesulfonic acid may be cited. It is proper to use a heavy metal salt such as silver perchlorate particularly when bromine is used as a leaving group of the sugar derivative. Properly, the reaction temperature is in the range of 5–30° C., preferably 10–25° C. and the reaction time is in the range of 12–48 hours, preferably 20–30 hours.

The chromanol glucoside aimed at is then obtained by purifying the resultant reaction product as by silica gel column chromatography and depriving the purified reaction product of the protective group as with sodium hydroxide or methanol.

The chromanol glucoside which is obtained by the enzyme method or the organic synthesis method described above is generally is an amphoteric molecule possessing very high water-solubility (about 100 g/100 ml) and abounding in oil solubility (octanol/water type distribution coefficient >3). In other words, the chromanol glucoside according to this invention may be called a water-soluble vitamin E endowed with high lipid affinity. Unlike the conventional vitamin E derivative which is insoluble or sparingly soluble in water, the chromanol glucoside according to this invention retains high lipid affinity even when it is used as dissolved in water. Since it is capable of permeating cell membranes and entering cell interiors, it immensely ameliorates the conditions of inflammatory bowel diseases by reinforcing the antioxidation preventing system in the organism and effectively repressing and controlling the free radical reactions on the intestinal mucous membrane in trouble. Further, the chromanol glucoside which is obtained by the reaction described above is greatly improved in thermal stability and pH stability over tocopherol, Trolox, or 2-substituted alcohol.

The preventive and curative agent for inflammatory bowel diseases according to this invention which is obtained by compounding the aforementioned chromanol glucoside with a pharmaceutically allowable carrier can be given to a patient as a composition for oral administration or not for oral adimindistration. In the case of the oral administration of the present agent, the chromanol glucoside mentioned above may be suitably mixed with suitable additives such as, for example, excipients like milk sugar, cane sugar, mannit, corn starch, synthetic or natural gum, and crystalline cellulose, binding agents like starch, cellulose derivatives, gum arabic, gelatin, and polyvinyl pyrrolidone, disintegrators like carboxymethyl cellulose calcium, carboxymethyl cellulose sodium, starch, corn starch, and sodium alginate, lubricants like talc, magnesium stearate, and sodium stearate, and fillers or diluents like calcium carbonate, sodium carbonate, calcium phosphate, and sodium phosphate and molding the resultant mixtures in solid preparations such as tablets, dust (powder), pills, and granules.

Alternatively, the chromanol glucoside may be manufactured into capsules by the use of soft gelatin capsules. The solid preparations may be vested with an enteric coating by the use of a coating substrate such as hydroxypropyl methyl cellulose phthalate, hydroxypropyl methyl cellulose acetate succinate, cellulose acetate phthalate, or methacrylate copolymer. The chromanol glucoside mentioned above can be manufactured into a liquid preparation such as syrup or elixir when it is dissolved in an inert diluent generally used as in purified water and, when necessary, a wetting agent, an emulsifier, a dispersion auxiliary, a surfactant, an edulcorant, a flavor, an aromatic substance, and the like are suitably added to the resultant solution.

When the preventive and curative agent of this invention for inflammatory bowel diseases is intended for nonoral administration, the chromanol glucoside mentioned above may be suitably combined with purified water, a suitable buffer such as phosphate buffer, physiological saline water, Ringer's solution, a physiological salt solution such as Locke's solution, ethanol, glycerin, and a popularly used surfactant to produce a sterilized aqueous solution, nonaqueous solution, suspension, ribosome, or emulsion. The liquid preparation is preferably administered intravenously, hypodermically, intramuscularly, intraabdominally, or intestinally in the form of a sterilized injection-grade aqueous solution. Properly, this liquid preparation has a physiological pH value, preferably in the range of 6–8.

Further, the preventive and curative agent of this invention for inflammatory eteropathic diseases may be administered in the form of an inserting pellet or a suppository.

The mode of administration and the path of administration are selected appropriately from among those described or suggested above by the physician in charge of medication.

The concentration of the chromanol glucoside contained in the preventive and curative agent of this invention for inflammatory bowel diseases, though variable with such factors as the form of agent ready for administration, the kind and seriousness of disease, and the target amount of the administration, generally falls in the range of 0.1–100 wt. %, preferably 20–90 wt. %. Particularly when the agent is orally administered, this concentration is in the range of 10–200 wt. %, preferably 20–90 wt. %, based on the total weight of the raw material. When it is administered nonorally, the concentration is in the range of 0.1–90 vol. %, preferably 1–80 vol. %, based on the total volume of the raw material. If the concentration of the chromanol glucoside exceeds the upper limit of the range mentioned above, the excess will fail to bring a proportionate increase in the effect of ameliorating the condition of disease. If the concentration of the chromanol glucoside is less than the lower limit of the range mentioned above, the shortage will prevent the effect of amelioration of the condition of disease from being satisfactory as expected.

The amount of administration of the preventive and curative agent of this invention for inflammatory bowel diseases varies with such factors as the age of a patient, the body weight and the symptom of the patient, the target mode and method of administration, the effect of cure, and the duration of medication and it ought to be accurately determined by the physician in charge of the medication. Generally, however, the amount of the chromanol glucoside to be administered is in the range of 0.01–10000 mg/kg of body weight/day. When the preventive and curative agent of this invention for inflammatory bowel diseases is orally administered, the dosage reduced to the amount of chromanol glucoside to be administered is in the range of 0.1–10000 mg/kg of body weight/day, one through three times per day. When the amount to be orally administered per day is unduly large, the agent may be dispensed in the form of tablets, which are suitably taken as apportioned into several pieces per dose. When the preventive and curative agent of this invention for inflammatory bowel diseases is nonorally administered, the dosage reduced to the amount of chromanol glucoside to be administered is in the range of 0.1–1000 mg/kg of body weight/day, one through three times per day.

Now, the pharmacologic effect of the preventive and curative agent of this invention for inflammatory bowel diseases will be described more specifically below with reference to a pharmacological test performed by the use of animals.

Effect of Repressing Lesion in TNB-Induced Colitis

The trinitrobenzenesulfonic acid (TNB)-induced colitis is said to resemble the inflammatory bowel disease of man, particularly Crohn's disease. In this model, the myeloperoxidase (MPO) activity, i.e. an index of the humectation of neutrophil into the tissue, prominently increases in the intestinal mucous membrane from the initial stage of the TNB administration onward and thereafter induces full-thickness inflammations inclusive of edema, erosion, and necrosis of the intestinal duct. In this lesion of the mucous membrane, the thiobarbituraic acid (TAB) reaction substance, i.e. an index of the peroxide of lipid, also increases and the antioxidizing substances such as the SOD activity, the glutathionperoxidase (GPx) activity, and α-tocopherol conversely decrease. By the use of this model, the chromanol glucoside was tested for the effect thereof manifested in repressing the lesion of the TNB-induced colitis.

As the chromanol glucoside, the 2-(α-D-glucopyranosyl) methyl-2,5,7,8-tetramethylchroman-6-ol (TMG) represented by the following formula (3) produced by the method described in Example 1 of JP-A-07-118,287 was thoroughly dissolved in water in varying concentrations of 20 mg/ml, 2 mg/ml, and 0.2 mg/ml to obtain injection grade preparations.

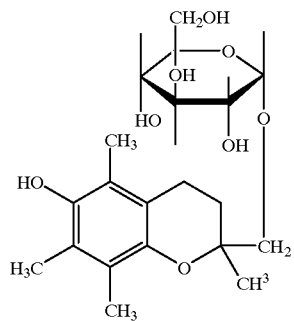

(3)

Male Wistar rats 7 weeks old weighing 190–210 g were divided into groups of six heads. To the rats, after 48 hours' fasting, the TBN dissolved in 50% ethanol in a ratio of 120 mg/ml was intestinally administered at a dose of 1 ml/kg. Thereafter, the TMG preparations obtained as described above were administered to the rats intraabdominally at a dose of 1 lm per head daily. After one week of the administration, the rats were rated for increase of body weight, damage score of the intestine in a 8 cm region on the side of the anus, wet weight, TBA reactive substance, and MPO activity.

These results are shown in Table 1 and Table 2 together with the results obtained of the normal group to which physiological saline water was administered in the same amount in the place of the TNB and of the control group to which physiologically saline water was administered in the same amount in the place of the TMB preparation subsequently to the induction of the TNB colitis. Of the items of rating mentioned above, the damage score, the TBA reactive substance, and the MPO activity were measured by the following methods.

(1) Method for Rating Damage Score

The lesion on the intestinal mucous membrane was classified on the six-point (0–5) scale in accordance with the Morris Classification (G. P. Morris, et al.,: Gastoenterology, 96 (1989) 750–803) and the degree of adhesion to the intestinal mucous membrane was classified on the four-point (0–3) scale (0: absence of adhesion, 1: presence of incontinuous adhesion, 2: presence of continuous adhesion, and 3: presence of clots). The sums of these points were used for rating.

(2) Method for Determination of TBA Reactive Substance

The determination was performed in accordance with the method proposed by Ohkawa et al. (H. Ohkawa, et al.: Anal. Biochem., 95 (1979) 351–358). The mucous membrane, 8 cm in length, of a given intestine was homogenized with 1.5 ml of (10 mM phosphate buffer+30 mM of potassium chloride solution). A 0.2-ml portion of the resultant homogenate, 0.6 ml of distilled water, 0.2 ml of 8.1% sodium disulfate, 1.5 ml of 20% acetate buffer having a pH of 3.5, 1.5 ml of 0.8% TBA, and 40 $\mu$l of 2% BHT added thereto were together heated at 95° C. for one hour. The resultant hot mixture was cooled for 10 minutes. The mixture and 1.0 ml of distilled water and 5.0 ml of butanol pyridine (ratio of butanol to pyridine=15:1) added thereto were together stirred. The stirred mixture was centrifuged at 3000 rpm at room temperature for 10 minutes. The supernatant resulting from the centrifugation was measured for absorbance at a wavelength of 535 nm with a spectrophotometer. From a blank using 0.8 ml of distilled water in the place of 0.2 ml of the homogenate of intestinal mucous membrane and a standard using 0.3 ml of distilled water and 0.5 ml of TEP, a calibration curve was obtained. Based on this calibration curve, the TBA reactive substance of a sample was determined.

(3) Method for Determination of MPO Activity

The determination was carried out in accordance with the o-dianisidine-hydrogen peroxide reaction (J. E. Krrawisz, et al.,: Gastoenterology, 87 (1984) 1344–135). A portion, 8 cm in length, of the mucous membrane of the intestine was homogenized with 1.5 ml of (10 mM phosphate buffer+30 mM potassium chloride solution). A portion, 1.0 ml in volume, of the resultant homogenate was supercentrifuged at 4° C., at 15000 rpm for 15 minutes. The resultant sediment was redissolved in 300 $\mu$l of 0.5% HTB (50 mM phosphate solution) added thereto. The produced solution was further centrifuged at 4° C., at 15000 rpm for 15 minutes. The resultant supernatant was used as a sample. In 950 $\mu$l of a reaction solution prepared by dissolving 16.7 mg of o-dianidine dihydrochloride in 50 mM of potassium phosphate having a pH of 6.0 and further mixing the resulting solution with 100 $\mu$l of an aqueous 0.5% hydrogen peroxide solution, 50 $\mu$l of the sample was placed and measured for change in absorbance at a wavelength of 460 nm with a spectrophotometer. The amount of MPO required for varying 1 $\mu$mol of the aqueous hydrogen peroxide solution at 25° C. for one minute was used as one unit (U).

TABLE 1

| | | Amount of increase in body weight (g/one week) | Damage score | Wet weight (g/8 cm) |
|---|---|---|---|---|
| Normal group | | 93.5 | 0 | 0.58 |
| Control group | | 17.5 | 7.25 | 2.6 |
| TMG administration group | 20 mg/ml | 57 | 4 | 0.86 |
| | 2 mg/ml | 64 | 3.75 | 1.15 |
| | 0.2 mg/ml | 63 | 4.75 | 1.06 |

TABLE 2

| | | TAB reactive substance (ng/mg protein) | MPO activity (U/l/mg protein) |
|---|---|---|---|
| Normal group | | 0.13 | 0.19 |
| Control group | | 0.53 | 0.74 |
| TMG administration group | 20 mg/ml | 0.35 | 0.48 |
| | 2 mg/ml | 0.38 | 0.64 |
| | 0.2 mg/ml | 0.31 | 0.52 |

It is clearly noted from Table 1 and Table 2 that the increase in body weight during one week was conspicuously repressed in the model of TNB-induced colitis (control group) and this phenomenon of repression was alleviated in the TMG preparation administration group. While the damage score, wet weight, TBA reactive substance, and MPO activity were invariably increased conspicuously in the model of TNB-induced colitis, these increases were significantly repressed in the TMG preparation administration group.

Test for Acute Toxicity

The preventive and curative agent of this invention for inflammatory bowel diseases was tested for acute toxicity in an effort to confirm the safety thereof. ICR type mice 4–5 weeks old were divided into groups of three heads. The same TMG as mentioned above was suspended as a chromanol glucoside in 5% gum arabic solution. The resultant suspension was orally administered to the rats in a dosage of 500 mg/kg as reduced to TMG, with the rats kept under observation for one week. In this case, 0.3 ml of a 5% gum arabic solution was administered to a control group. No case of death of mouse was found in any of the groups of administration.

INDUSTRIAL APPLICABILITY

The preventive and curative agent for inflammatory bowel diseases according to this invention can repress the lesions in the inflammatory bowel diseases and notably ameliorate the conditions of the diseases because it has as an active ingredient the chromanol glucoside not merely possessing fine antioxidization resisting action and free radical resisting action but also exhibiting an action of repressing the development of cell adhesion molecules and significantly repressing the humectation of neutrophil into the intestinal tissue.

Further, the preventive and curative agent according to this invention, owing to the use of the chromanol glucoside possessing high water solubility as the active ingredient, can be used not only as a solid preparation but also as an aqueous preparation containing the active ingredient at a high concentration. The agent, therefore, acts effectively on the seat of disease at a low application rate and prevents and cures inflammatory bowel diseases. Moreover, it can be used very safely because it entails no side effect.

What is claimed is:

1. A method for the prevention or treatment of inflammatory bowel diseases comprising the step of administering to a patient in need thereof an effective amount of a composition comprising a preventative or treatment agent for inflammatory bowel disease having as an active ingredient thereof a chromanol glucoside represented by the following general formula (1)

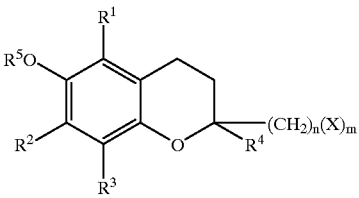

(1)

(wherein $R^1$, $R^2$, $R^3$, and $R^4$ represent identically or differently either a hydrogen atom or a lower alkyl group, $R^5$ represents a hydrogen atom, a lower alkyl group, or a lower acyl group, X represents a monosaccharide residue or an oligosaccharide residue having the hydrogen atom in the hydroxyl group thereof optionally substituted with a lower alkyl group or a lower acyl group, n represents an integer of 0–6, and m represents an interger of 1–6).

2. The method according to claim 1, wherein said chromanol glucoside is 2-($\alpha$-D-glucopyranosyl)methyl-2,5,7,8-tetramethylchroman-6-ol.

3. The method according to claim 1, wherein said inflammatory bowel disease is an ulcerative colitis or Crohn's disease.

4. The method according to claim 1, wherein said composition is an aqueous preparation.

5. The method of claim 1, wherein the composition further comprises a carrier.

* * * * *